United States Patent [19]
MacLean et al.

[11] Patent Number: 6,017,964
[45] Date of Patent: Jan. 25, 2000

[54] METHOD OF INCREASING TESTOSTERONE

[75] Inventors: David B. MacLean, Providence, R.I.; David D. Thompson, Gales Ferry, Conn.

[73] Assignee: Pfizer Inc., New York, N.Y.

[21] Appl. No.: 09/208,729

[22] Filed: Dec. 9, 1998

Related U.S. Application Data

[63] Continuation of application No. 08/803,711, Feb. 21, 1997, abandoned.
[60] Provisional application No. 60/021,181, Feb. 28, 1996.

[51] Int. Cl.$^7$ ................................................ A61K 31/135
[52] U.S. Cl. .......................................................... 514/648
[58] Field of Search ............................................. 514/648

[56] References Cited

U.S. PATENT DOCUMENTS

| | | | |
|---|---|---|---|
| 5,047,431 | 9/1991 | Schickaneder et al. | 514/648 |
| 5,254,594 | 10/1993 | Kazuaki et al. | 514/648 |
| 5,384,332 | 1/1995 | Fontana | 514/648 |
| 5,389,670 | 2/1995 | Fontana | 514/443 |
| 5,441,986 | 8/1995 | Thompson | 514/648 |
| 5,455,275 | 10/1995 | Fontana | 514/648 |
| 5,550,164 | 8/1996 | Fontana | 514/648 |

OTHER PUBLICATIONS

Ke, et al., Bone, 20, pp. 31–39 (1997).
Geisler, et al., J. Endocrinol., 146(2), pp. 359–363 (1995).
Lonning, et al., J. Steroid Biochem, Molec. Biol., 52(5), pp. 491–496 (1995).
Hasmann, et al., Cancer Letters, 84, pp. 101–116 (1994).
Morley, et al., Jags, 41, pp. 149–152 (1993).
Wiseman, et al., Cancer Letters, 66, pp. 61–68 (1992).
Eppenberger, et al., Am. J. Clin. Oncol., 14, pp. S5–S14 (1991).
Kvinnsland, S., J. Cancer Res. Clin. Oncol., 116(Suppl. Part 2), p. 930 (1990).
Grant & Hackh's Chemical Dictionary, Fifth Edition, p. 37 (1987).
Lewis–Jones, et al., Andrologia, 19(1), p. 86–90 (1987).
Van Bergeijk, et al., Horm. Metabol. Res., 18, pp. 558–564 (1986).

*Primary Examiner*—Jerome D. Goldberg
*Attorney, Agent, or Firm*—Peter C. Richardson; Paul H. Ginsburg; Mark Dryer

[57] ABSTRACT

The present invention provides novel methods of increasing serum levels of testosterone comprising administering to a mammal in need of such treatment an effective amount of a compound of formula I

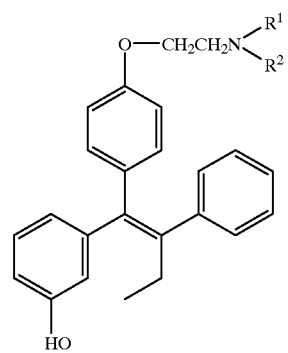

(I)

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof.

3 Claims, No Drawings

METHOD OF INCREASING TESTOSTERONE

This is a continuation of Ser. No. 803,711, filed Feb. 21, 1997, now abandoned which is a continuation of provisional application 60/021,181 filed Feb. 28, 1996 the benefit of which is hereby claimed under 37 C.F.R. §1.78(a)(3).

BACKGROUND OF THE INVENTION

In males, small amounts of estrogen are produced by aromatization of testosterone both in the testes and peripheral tissues. Although present in only small amounts, generally less than one-fourth to one-tenth that in premenopausal women, estrogen may play a role in the regulation of the male hypothalamic pituitary gonadaxis, bone development, development of the prostate and metabolic function. In the hypothalamus, conversion of testosterone to estrogen results in negative feedback on gonadotropin releasing hormone and subsequent gonadotropin release. Estrogens thus normally reduce circulating testosterone and anti-estrogens result in corresponding increases. As men age, the proportion of fat to lean tissue gradually increases. Aromatization of testosterone in fat may lead to gradually increased estrogen to testosterone ratios and negative feedback that reduces total testosterone levels.

Hypogonadism is recognized as a common occurrence in older males. A number of studies have suggested that hypogonadism may result in some of the observed decrements in muscle and skeletal mass associated with advancing age. Recent studies have suggested that androgen therapy produces a small but significant improvement in muscle strength in eugonadal males. Testosterone deficiency has been associated with hip fracture, and bone mass has been correlated with testosterone levels in older persons.

Males who received testosterone had a significant increase in bioavailable testosterone concentration, hematocrit, right hand muscle strength and osteocalcin concentration. They had a decrease in cholesterol (without a change in HDL-cholesterol) levels and decreased BUN/Creatinine ratios. Morley, et al. *JAGS* 41:149–152 (1993).

The estrogen antagonist tamoxifen has been used in males to treat advansced breast cancer. Treatment with tamoxifen has been shown to increase serum levels of testosterone in both mammal and oligozoospermic men. (Lewis-Jones, et al., andrologia 19 (1):86–90 (1987)). In addition, the anti-estrogen clomiphene is used to treat decreased libido, hypogonadotrophic hypogonadism and associated infertility. A potential role for anti-estrogens in the older male has not been systematically evaluated.

Droloxifene (Formula I, below, $R^1$, $R^2$=methyl) is a new tissue-specific estrogen agonist/antagonist that is being developed for the treatment of advanced breast cancer and osteoporosis. Although droloxifene has been studied in a few men with advanced colon or pancreatic cancer, its endocrine effects in the normal male have not been studied. Droloxifene is chemically related to tamoxifen, but in preclinical studies in rats is devoid of tamoxifen's hepatocarcinogicity. In humans, droloxifene has a superior pharmacokinetic profile with fewer, inactive, metabolites a shorter half life of 24 hours (vs. tamoxifen's 1 to 2 weeks and multiple metabolites).

SUMMARY OF THE INVENTION

The present invention relates to methods for increasing serum levels of testosterone comprising administering to a mammal in need of such treatment an effective amount of a compound of formula I

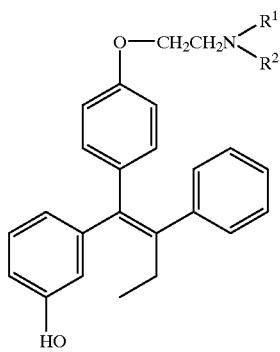

(I)

wherein
$R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof. A preferred compound of formula I is that in which $R^1$ and $R^2$ are methyl. A preferred salt is the citrate salt.

DETAILED DESCRIPTION OF THE INVENTION

The present invention concerns methods for increasing serum levels of testosterone in a mammal. The present methods include both medical therapeutic and/or prophylactic treatment, as appropriate. Low testosterone levels, especially in the elderly, may lead to frailty, impotence and lowered libido.

The methods of this invention are practiced by administering to an individual in need of treatment an effective amount of a compound formula I

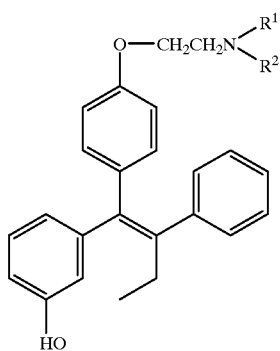

(I)

wherein
$R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof.

Compounds of formula I are known in the art and essentially are prepared via the methods described in U.S. Pat. No. 5,047,431, which is hereby incorporated herein by reference.

A preferred formula I compound is that in which $R^1$ and $R^2$ each are methyl. This preferred compound is known as droloxifene which previously has been described as an antiestrogenic agent and is useful for the treatment of hormone dependent mammary tumors (U.S. Pat. No. 5,047, 431), and for the relief of bone diseases caused by the deficiency of estrogen or the like (U.S. Pat. No. 5,254,594). Furthermore, droloxifene is known to have less uterotrophic effect than other antiestrogenic compounds such as tamoxifen.

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydrolodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalate-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds can be administered to an individual in need of treatment for the methods herein described. The following nonlimiting test examples illustrate the methods of the present invention.

For the methods of the present invention, compounds of Formula I are administered continuously, or from 1 to 4 times daily.

As used herein, the term "effective amount" means an amount of compound of the methods of the present invention which is capable of inhibiting the symptoms of the pathological conditions herein described. The specific dose of a compound administered according to this invention will, of course, be determined by the particular circumstances surrounding the case including, for example, the compound administered, the route of administration, the state of being of the patient, and the severity of the pathological condition being treated. A typical daily dose will contain a nontoxic dosage level of from about 0.25 mg to about 100 mg/day of a compound of the present invention. Preferred daily doses generally will be from about 10 mg to about 40 mg/day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Typically, a formula I compound, or a pharmaceutically acceptable salt thereof, is combined with a pharmaceutically acceptable carrier, diluent or excipient to form a pharmaceutical formulation.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate agents for retarding dissolution such as paraffin resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elbdrs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I generally will be administered in a convenient formulation. The following formulation examples only are illustrative and are not intended to limit the scope of the present invention.

In the formulations which follow, "active ingredient" means a compound of formula 1, or a salt thereof.

Formulation 1: Gelatin Capsules

Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–50 |
| Silicon dioxide, fumed | 10–650 |
| Stearate acid | 5–15 |

The components are blended and compressed to form tablets.

Alternatively, tablets each containing 0.25–100 mg of active ingredient are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of medicament per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The medicament is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient | 20 mg |
| Isotonic saline | 1,000 mL |

The solution of the above ingredients is intravenously administered to a patient at a rate of about 1 mL per minute.

Test Method

Sixty generally healthy men between the ages of 62 to 75 are selected for evaluation based on the following criteria:

Inclusions

1. Body weight between 90 and 130% of the mid-range of ideal body weight as defined by the Metropolitan Life Insurance Table (Appexdix 1) for men of average frame.

2. Serum testosterone at screening less than 500 ng/dl.

3. Serum prostate specific antigen for less than or equal to 4 ng/ml.

4. Normal clinical prostate exam and the absence of suspicious nodules on creening prostate ultrasound.

5. No significant act of medical illnesses such as angina, myocardial infarction or angioplasty within the past 2 years, history of visceral cancer within the previous 5 years or prostate cancer at any time.

6. Normal physical examination at screening, including normal cardiopulmonary exam, absence of peripheral vascular or venus disease, or other evidence of systemic disease.

7. The following must be within 10% of the upper or lower range limits of normal as reported by the reference laboratory: CBC, including hemoglobin, hematocrit and total WBC.

Exclusions

1. Men who smoke

2. Men with a previous history of thromboembolic disease or pulmonary embolus at any time in the past.

3. Men who consume more than 2 units of alcohol per day, equivalent to approximately 2 glasses of wine, 2 bottles of beer.

4. Clinically significant abnormalities on screening electrocardiogram.

The study is of parallel design and placebo controlled comparing two doses of a compound of formula I at 10 and 40 mg/day vs. placebo for 14 weeks. Subjects are randomized to compound or placebo. Testosterone levels are measured every two weeks with the RIA, Coat-a-Count Kit available from Diagnostic Products Co. 5700 W. 96th Street, Los Angeles, Calif. 90045. A statistically significant increase in testosterone levels over the placebo indicates that a compound of formula I is effective in increasing serum testosterone.

We claim:

1. A method for increasing serum levels of testosterone in a male mammal comprising administering to a male mammal in need of such treatment an effective amount of a compound of formula I

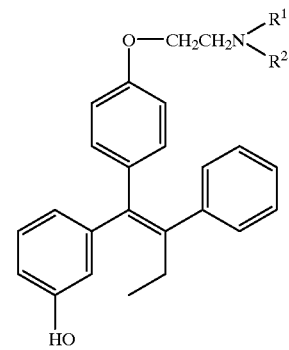

wherein
$R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof.

2. A method according to claim 1 wherein the compound of formula I is a compound wherein $R^1$ and $R^2$ each are methyl, or a pharmaceutically acceptable salt thereof.

3. A method according to claim 2 wherein said salt thereof is the citrate salt.

* * * * *